(12) United States Patent
DiPerna et al.

(10) Patent No.: US 10,709,343 B2
(45) Date of Patent: Jul. 14, 2020

(54) COMPUTER-BASED SYSTEMS AND METHODS FOR MONITORING THE HEART MUSCLE OF A PATIENT WITH CONTEXTUAL OVERSIGHT

(71) Applicant: NATIONAL CARDIAC, INC., Escondido, CA (US)

(72) Inventors: Paul M. DiPerna, Escondido, CA (US); Freeman H. Rose, Jr., Del Mar, CA (US)

(73) Assignee: National Cardiac, Inc., Solana Beach, CA (US)

( * ) Notice: Subject to any disclaimer, the term of this patent is extended or adjusted under 35 U.S.C. 154(b) by 353 days.

(21) Appl. No.: 15/665,020

(22) Filed: Jul. 31, 2017

(65) Prior Publication Data

US 2019/0029545 A1    Jan. 31, 2019

(51) Int. Cl.
| | | |
|---|---|---|
| *A61B 5/024* | (2006.01) | |
| *G06F 19/00* | (2018.01) | |
| *G16H 40/63* | (2018.01) | |
| *A61B 5/00* | (2006.01) | |
| *G16H 50/20* | (2018.01) | |
| *A61B 5/0432* | (2006.01) | |

(52) U.S. Cl.
CPC ........ *A61B 5/02438* (2013.01); *A61B 5/0432* (2013.01); *A61B 5/7275* (2013.01); *G06F 19/3418* (2013.01); *G16H 40/63* (2018.01); *G16H 50/20* (2018.01); *A61B 2560/0247* (2013.01)

(58) Field of Classification Search
CPC ...... A61L 27/3604; A61L 27/50; A61L 27/58; A61L 27/54; A61L 27/3691; A61L 27/3683; A61L 2300/60; A61L 2300/412; A61L 2430/40; A61K 35/50
See application file for complete search history.

(56) References Cited

U.S. PATENT DOCUMENTS

| | | |
|---|---|---|
| 3,412,729 A | 11/1968 | Smith, Jr. |
| 6,225,901 B1 | 5/2001 | Kail, IV |
| 6,569,095 B2 | 5/2003 | Eggers |
| 6,940,403 B2 | 9/2005 | Kail, IV |
| 7,212,850 B2 | 5/2007 | Prystowsky |
| 7,587,237 B2 | 9/2009 | Korzinov |
| 7,907,996 B2 | 3/2011 | Prystowsky |
| 7,941,207 B2 | 5/2011 | Korzinov |
| 8,460,189 B2 | 6/2013 | Libbus |
| 8,463,376 B2 | 6/2013 | Curtis |

(Continued)

FOREIGN PATENT DOCUMENTS

EP       1304135 A2     4/2003

*Primary Examiner* — Mark Bockelman
(74) *Attorney, Agent, or Firm* — Nydegger & Associates

(57) ABSTRACT

A computer-based system for monitoring the heart muscle function of a patient, with contextual oversight, includes a sensor array for collecting physiological and environmental data that are pertinent to the patient. A context register is also included which contains periodically updated patient-specific data that establishes a relevant contextual oversight capability for the system. In operation, a computer identifies anomalies in the physical data and detects aberrations in the environmental data. These anomalies and aberrations are then interactively evaluated together, relative to the contextual oversight capability, to determine whether clinical intervention for the patient is warranted.

9 Claims, 1 Drawing Sheet

(56) References Cited

U.S. PATENT DOCUMENTS

| | | |
|---|---|---|
| 8,478,418 B2 | 7/2013 | Fahey |
| 8,620,418 B1 | 12/2013 | Kuppuraj |
| 8,744,561 B2 | 6/2014 | Fahey |
| 8,774,932 B2 | 7/2014 | Fahey |
| 8,798,734 B2 | 8/2014 | Kuppuraj |
| 2004/0059183 A1 | 3/2004 | Jansen |
| 2007/0255379 A1 | 11/2007 | Williams |
| 2007/0287880 A1 | 12/2007 | Ovil |
| 2007/0288070 A1 | 12/2007 | Libbus |
| 2010/0042185 A1 | 2/2010 | Curtis |
| 2010/0087744 A1 | 4/2010 | Licata |
| 2012/0101476 A1 | 4/2012 | Curtis |
| 2017/0087342 A1 | 3/2017 | Curtis |

COMPUTER-BASED SYSTEMS AND METHODS FOR MONITORING THE HEART MUSCLE OF A PATIENT WITH CONTEXTUAL OVERSIGHT

FIELD OF THE INVENTION

The present invention pertains to systems and methods for monitoring the heart muscle function of a patient for the purpose of evaluating the health and wellbeing of the patient. More particularly, the present invention pertains to systems and methods that monitor and evaluate physiological and environmental data in light of patient-specific data, to consider the interaction of all pertinent factors that affect the health and wellbeing of the patient. The present invention is particularly, but not exclusively, useful for systems and methods that provide a contextual oversight capability for evaluating a patient's heart muscle function.

BACKGROUND OF THE INVENTION

It is well known that there is a plethora of different types of sensors which can detect or measure physical phenomena. Each sensor is specifically designed to make a particular measurement, although the measurement itself may be used for different purposes. Moreover, it is well known that an array of different sensors can be used to simultaneously measure different aspects of a single entity from different perspectives (e.g. speed, fuel level and engine oil temp of an automobile). It is an altogether different matter, however, when several different sensors need to be collectively and interactively considered electronically to develop a consensus, or determine a particular course of action, which simply cannot be done by a single sensor.

With the above in mind, consider the situation that is presented when it is desirable, or necessary, to monitor and evaluate the heart muscle function of a patient. In overview, a thorough and comprehensive protocol for monitoring and evaluating a patient's heart muscle requires the collective consideration of physiological factors, environmental factors and contextual matters. Further, to be truly meaningful, a consideration of these factors also requires an evaluation of how they interact with each other.

It is well known that an electrocardiogram (EKG) is capable of accurately recording the waveform of a heart muscle function. Furthermore, there are trained clinicians who can interpret the EKG waveform to identify and diagnose many different heart muscle irregularities. Thus, insofar as physiological factors are concerned, an EKG-type sensor can continuously provide valuable physiological data that is pertinent to the heart muscle. Using only EKG data, however, may be limiting.

In addition to the physiological factors that can be measured by an EKG (i.e. heart muscle waveform parameters), it is known that environmental factors (i.e. external influences) can also significantly affect the waveform of a patient's heart muscle function. For instance, temperature, weather conditions, trauma, time of day and situational perceptions are all environmental factors that may necessarily need to be taken into account. These external influences, however, cannot be detected by an EKG, per se. Moreover, environmental factors tend to be episodic and of relatively short duration. Nevertheless, their effect on the heart muscles can have long lasting consequences. In any event, sensors, other than an EKG, such as accelerometers, thermometers, audiometers and potentiometers, are more appropriate for measuring and detecting the impact of environmental factors.

In addition to the above, the overall general health and wellbeing of a patient will also affect his/her heart muscle function. Thus, patient data, to include medical records, behavioral patterns, care plans, and clinical perceptions, are factors that need to be considered along with physiological and environmental factors. It is also an important consideration that, unlike the physiological and environmental data that can be continuously monitored, the collection of patient data will necessarily require frequent updating.

In light of the above, it is an object of the present invention to provide a system and method for monitoring the heart muscle function of a patient with contextual oversight that interactively considers the effect that physiological, environmental, and patient-specific factors will collectively have on the health and wellbeing of a patient. Another object of the present invention is to provide a system and method for monitoring the heart muscle function of a patient that allows for periodic updates of patient-specific data to provide for a contextual oversight of a heart monitoring protocol. Still, another object of the present invention to provide a system and method for monitoring the heart muscle function of a patient that is easy to use, is simple to incorporate, and is comparatively cost effective.

SUMMARY OF THE INVENTION

In accordance with the present invention, a computer-based system is provided with a contextual oversight capability for monitoring the heart muscle function of a patient. In combination the system includes a sensor array for collecting physiological and environmental data, a context register for storing patient-specific data, and a computer for evaluating all of the collected data from the sensor array in light of data from the context register to determine whether a clinical intervention is warranted. As envisioned for the present invention, these components will interactively cooperate with each other to assess the overall health and wellbeing of a patient.

With regard to the sensor array of the present invention, it includes a cardiac sensor for collecting cardiac input data that is pertinent to physiological aspects of a patient. It also includes at least one perturbation sensor for collecting perturbation input data that is pertinent to environmental factors influencing the patient. Preferably, the cardiac sensor is an electrocardiogram (EKG) and each perturbation sensor is selected from the group consisting of accelerometers, thermometers, audiometers and potentiometers, depending on the needs of the patient. In addition to the sensor array, a context register is provided for periodically receiving and storing patient data. In detail, the patient data will include medical records of the patient, routine behavioral patterns of the patient, a care plan for the patient, and clinical perceptions recorded by physicians and staff pertinent to the patient needed to maintain a relevant context for the patient. Due to the nature of the patient data, the context register will necessarily be configured to periodically receive updated patient data.

For an operation of the present invention, the computer is provided to receive physiological data input from the cardiac sensor in the sensor array, and to then evaluate this data to identify anomalies. For this evaluation purpose, the computer is pre-programmed with a cardio-profile. In particular, the cardio-profile establishes predetermined acceptable ranges, R, for variations of individual parameters that are received in the cardiac input data. Accordingly, when an individual parameter in the cardiac input data extends beyond an acceptable range R in the cardio-profile, an anomaly is identified for a physiological factor. For purposes of the present invention, the parameters evaluated with the cardio-profile are based on a waveform of the heart muscle, and are selected from the group consisting of: waveform shape characteristics, amplitudes within the waveform, the repetition rate of heart function cycles in the waveform variability of the waveform shape, discontinuities in the waveform and variability of the repetition rate.

In addition to the cardio-profile disclosed above, the computer is also pre-programmed with a response matrix. Specifically, the response matrix will include a plurality of measurable parameters taken from external influences that have an effect on the patient. In the response matrix, each measurable parameter is assigned a weighting factor, W, according to the influence it may have on the cardiac input data. For the present invention, measurable parameters are selected from the group consisting of a magnitude, a duration, a trend, and a rate of change, together with variations and combinations thereof.

An analyzing unit is provided for the computer which includes a first analyzer that receives updated patient data from the context register, and then evaluates the data to determine whether a change order is required to alter the cardio-profile. If so, at least one of the ranges R for the cardio-profile is appropriately altered. Similarly, a second analyzer is provided for also receiving updated patient data from the context register to determine whether a change order, based on the updated patient data, is required to alter the response matrix. If a change is required, an alteration of at least one of the weighting factors W is made. In the event, based on updated patient data from the context register, anomalies identified from the sensor-data, relative to the cardio-profile, are compared with aberrations detected in the sensor-data, relative to the response matrix, to determine whether a clinical intervention or further inquiries are warranted.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
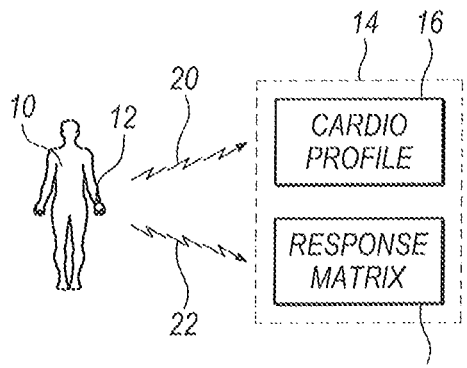
FIG. 1 is a schematic presentation of data flow from a patient to a computer in accordance with the present invention.

Referring initially to FIG. 1, a patient/user of the present invention is designated 10. As shown, the patient 10 is wearing a sensor array 12 that is connected in communication with a computer 14. For purposes of the present invention, the computer 14 can be either worn by the patient 10 together with the sensor array 12, or it can be located at a remote site (not shown).

As shown in FIG. 1, the computer 14 includes a cardio-profile 16, and a response matrix 18, which are both disclosed in detail in U.S. application Ser. No. 15/643,975 which was filed on Jul. 7, 2017 for an invention entitled "Cardiac Monitor with Perturbation Evaluation," which is incorporated herein by reference, and which is assigned to the same assignee as the present invention (hereinafter referred to as the '975 application). FIG. 1 also shows that the physiological data is transmitted from the patient 10 to the cardio-profile 16 in computer 14 via a communication link 20, and the data pertaining to external factors influencing the patient 10 is transmitted from the patient 10 to the response matrix 18 in computer 14 via a communication link 22.

For purposes of the present invention, the cardio-profile 16 is used to evaluate measurable parameters in cardiac input data from the patient 10. To do this, the cardio-profile 16 establishes acceptable ranges R for variations in individual parameters of the cardiac input data. In general, the measurable parameters are based on characteristics in a waveform of the heart muscle of the patient 10. Typically, they are selected from the group consisting of waveform shape characteristics, amplitudes within the waveform, the repetition rate of heart function cycles in the waveform, variability of the waveform shape, discontinuities in the waveform, and variability of the repetition rate. A more detailed disclosure of the cardio-profile is available with reference to the '975 application.

Like the cardio-profile 16, a more detailed disclosure of the response matrix 18 is also available with reference to the '975 application. In essence, the response matrix 18 includes measurable parameters that are taken from an external influence on the patient 10. Each measurable parameter is then given a weighting factor W according to the nature of its influence on the cardiac input data that is sent to the cardio-profile 16. Typically, measurable parameters are selected from the group consisting of: a magnitude, a duration, a trend, and a rate of change, together with variations and combinations thereof.

Figure 2:
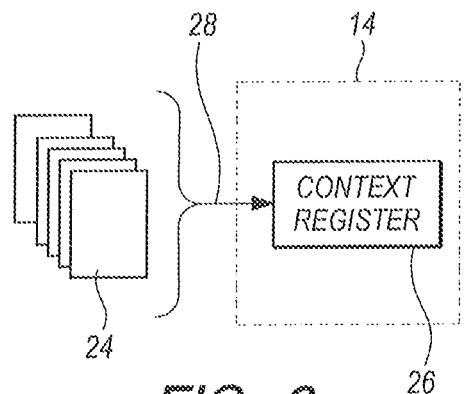
FIG. 2 is a schematic presentation of patient-specific data being input into a computer.

In FIG. 2 it is shown that, in addition to input for the cardio-profile 16 and the response matrix 18, patient data 24 is provided to a context register 26 via a communication link 28 for use by the computer 14. In particular, as intended for the present invention, the context register 26 will periodically receive and store patient data 24, including documented material such as medical records of the patient 10, routine behavioral patterns of the patient 10, a care plan for the patient 10, and clinical perceptions recorded by physicians and staff pertinent to the patient 10. This is done to continuously update patient data 24 that will collectively provide information in the patient data 24 that is needed to maintain a relevant context for the patient 10.

Figure 3:
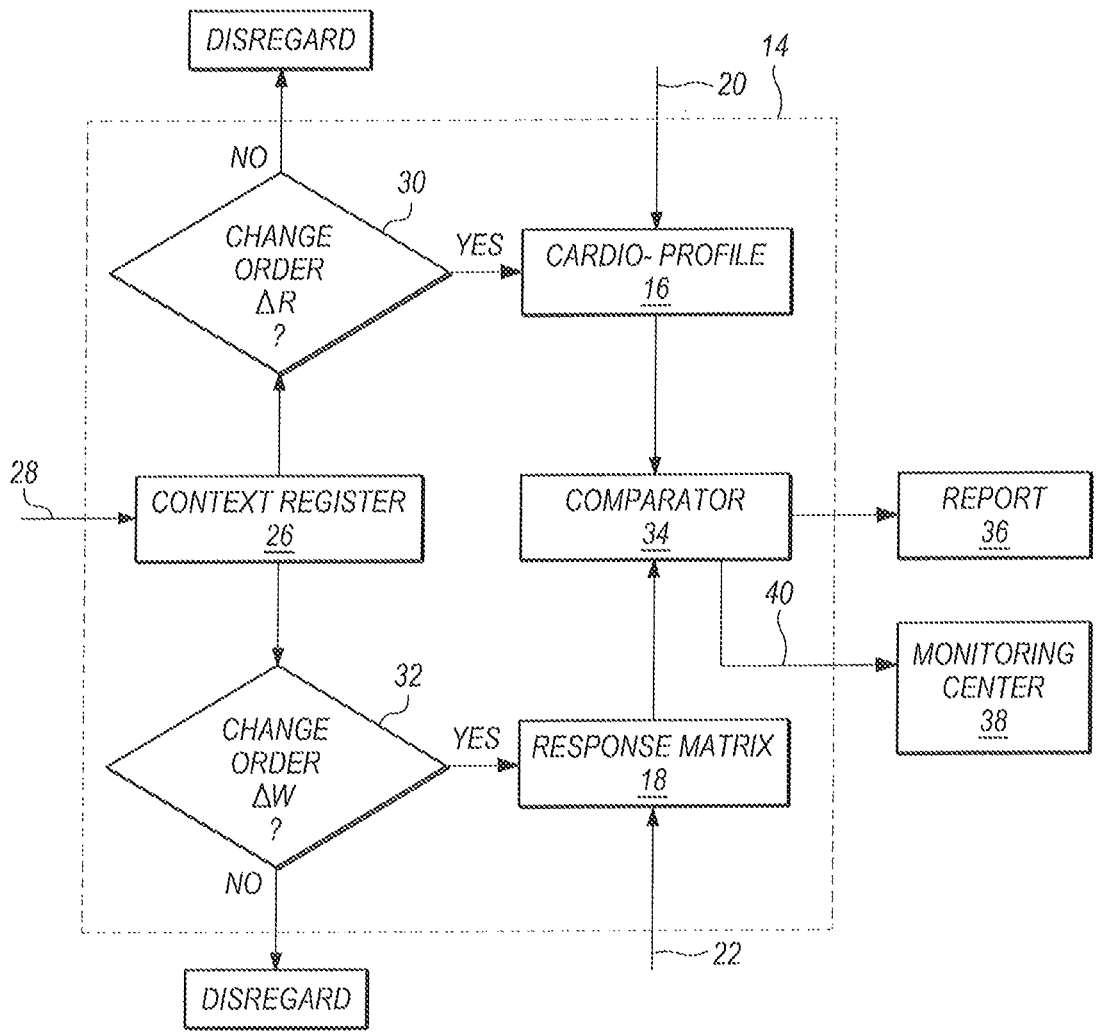
FIG. 3 is a functional diagram of the data manipulation tasks required for an operation of the present invention.

An operation of the present invention will be best appreciated with reference to FIG. 3 which shows the interactive tasks that are involved when manipulating data in accordance with the present invention. As shown in FIG. 3, input to the computer 14 includes: physiological data for evaluation by the cardio-profile 16, data pertaining to external influences affecting the patient 10 for evaluation by the response matrix 18, and patient data 24 to be incorporated into the context register 26 for use in updating the cardio-profile 16 and the response matrix 18.

In detail, FIG. 3 shows that the updating of the cardio-profile 16 and the response matrix 18 require separate analyses. For one, an analyzer 30 is used to determine whether patient data 24 in the context register 26 indicates the need for a change order to the cardio-profile 16. If so, this change order will involve an alteration of at least one of the ranges R in the cardio-profile 16. Specifically, such a change order may be required when an individual parameter in the cardiac input data extends beyond its acceptable range R in the cardio-profile 16. For another, an analyzer 32 is used to determine whether patient data 24 in the context register 26 indicates the need for a change order to the response matrix 18. In this case, a change order for the response matrix 18 involves an alteration of at least one of the weighting factors W.

Still referring to FIG. 3, it will be seen that updated patient data 24 for the cardio-profile 16 and the response matrix 18 is respectively provided by the analyzers 30 and 32. A comparator 34 then evaluates all of the collected data from the sensor array 12 in light of the pertinent changes that may be evidenced in the updated patient data 24. A report 36 can then be prepared which will indicate whether a clinical intervention is warranted.

In addition to the features disclosed above for the present invention, FIG. 3 also shows that a monitoring center 38 can be connected in communication with the computer 14. The purpose of the monitoring center 38 is to provide an oversight capability for continuously monitoring the interactive functions of the cardio-profile 16 and the context register 26. As shown in FIG. 3, the monitoring center 38 is connected to the comparator 34 of the computer 14 via a communication link 40.

While the particular Computer-Based Systems and Methods for Monitoring the Heart Muscle of a Patient with Contextual Oversight as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A computer-implemented system for monitoring the heart muscle function of a patient which comprises:
    a sensor array positionable on the patient for collecting physiological and environmental data pertinent to the patient;
    a cardio-profile for receiving the physiological data from the sensor array to manifest the physiological aspects of the heart muscle function of the patient;
    a response matrix for receiving the environmental data from the sensor array to manifest the external factors influencing the patient;
    a context register for storing patient data, wherein the patient data includes medical records of the patient, routine behavioral patterns of the patient, a care plan for the patient, and notes regarding perceptions recorded by physicians and clinical staff pertinent to the patient, wherein the patient data is continuously updated;
    a first analyzer for receiving updated patient data from the context register, wherein the first analyzer determines whether a change order based on the updated patient data is required to alter the cardio-profile;
    a second analyzer for receiving updated patient data from the context register, wherein the second analyzer determines whether a change order based on the updated patient data is required to alter the response matrix; and
    a comparator for comparing anomalies identified by the cardio-profile with aberrations detected by the response matrix, wherein the cardio-profile and the response matrix include alterations required by updated patient data from the context register, to evaluate the heart muscle function, and for generating
    a report based on the comparator evaluation, wherein the report is prepared for determining whether a clinical intervention is warranted.

2. The system of claim 1 wherein the sensor array comprises:
    a cardiac sensor for collecting cardiac input data; and
    at least one perturbation sensor for collecting perturbation input data.

3. The system of claim 2 wherein the cardio-profile includes measurable parameters from the cardiac input data and establishes acceptable ranges, R, for variations in individual parameters of the cardiac input data, and wherein the measurable parameters are based on a waveform of the heart muscle and are selected from the group consisting of waveform shape characteristics, amplitudes within the waveform, the repetition rate of heart function cycles in the waveform variability of the waveform shape, discontinuities in the waveform and variability of the repetition rate.

4. The system of claim 3 wherein a change order for the cardio-profile involves an alteration of at least one of the ranges R.

5. The system of claim 4 wherein an anomaly is identified when an individual parameter in the cardiac input data extends beyond an acceptable range R in the cardio-profile.

6. The system of claim 2 wherein the response matrix comprises:
    a plurality of measurable parameters taken from the perturbation input data, wherein each measurable parameter results from an external influence on the patient; and
    a plurality of weighting factors, W, wherein each characteristic of each measurable parameter is given a respective weighting factor W according to the influence the characteristic may have on the cardiac input data.

7. The system of claim 6 wherein characteristics of a measurable parameter are selected from the group consisting of: a magnitude, a duration, a trend, and a rate of change, together with variations and combinations thereof.

8. The system of claim 7 wherein a change order for the response matrix involves an alteration of at least one of the weighting factors W, and wherein the cardiac sensor is an electrocardiogram (EKG), and each perturbation sensor is selected from the group consisting of accelerometers, thermometers, audiometers and potentiometers.

9. The system of claim 1 further comprising a monitoring center connected with the comparator for monitoring the interactive functions of the cardio-profile and the response matrix.

* * * * *